US012672794B2

(12) United States Patent
Isogai et al.

(10) Patent No.: US 12,672,794 B2
(45) Date of Patent: Jul. 7, 2026

(54) LIVING-BODY MONITORING DEVICE

(71) Applicants:SEIKO GROUP CORPORATION, Tokyo (JP); SHOWA MEDICAL UNIVERSITY, Tokyo (JP)

(72) Inventors: Ryosuke Isogai, Matsudo (JP); Yoshifumi Yoshida, Matsudo (JP); Koutaro Maki, Tokyo (JP)

(73) Assignees: SEIKO GROUP CORPORATION, Tokyo (JP); SHOWA MEDICAL UNIVERSITY, Toyko (JP)

( * ) Notice: Subject to any disclaimer, the term of this patent is extended or adjusted under 35 U.S.C. 154(b) by 276 days.

(21) Appl. No.: 18/687,103

(22) PCT Filed: Aug. 24, 2022

(86) PCT No.: PCT/JP2022/031925
§ 371 (c)(1),
(2) Date: Feb. 27, 2024

(87) PCT Pub. No.: WO2023/032791
PCT Pub. Date:Mar. 9, 2023

(65) Prior Publication Data
US 2025/0127419 A1 Apr. 24, 2025

(30) Foreign Application Priority Data
Sep. 1, 2021 (JP) ................................. 2021-142568

(51) Int. Cl.
*A61B 5/07* (2006.01)
*A61B 5/00* (2006.01)
(Continued)

(52) U.S. Cl.
CPC ................ *A61B 5/07* (2013.01); *A61B 5/682* (2013.01); *H01Q 1/273* (2013.01); *H01Q 9/30* (2013.01)

(58) Field of Classification Search
None
See application file for complete search history.

(56) References Cited

U.S. PATENT DOCUMENTS

2003/0085994 A1 5/2003 Fujita et al.
2015/0102939 A1 4/2015 Hong et al.
2018/0000563 A1 1/2018 Shanjani et al.

FOREIGN PATENT DOCUMENTS

EP 2537492 A1 12/2012
JP 2003-135389 A 5/2003
(Continued)

OTHER PUBLICATIONS

Chandra et al. In-Mouth Antenna for Tongue Controlled Wireless Devices: Characteristics and Link-Loss; 33rd Annual International Conference of the IEEE EMBS Boston, Massachusetts USA, Aug. 30-Sep. 3, 2011 (Year: 2011).*
(Continued)

*Primary Examiner* — Jay B Shah
(74) *Attorney, Agent, or Firm* — Crowell & Moring LLP

(57) ABSTRACT
A living-body monitoring device includes an electronic device including a circuit board and a living-body wearing instrument fixing or sealing the electronic device. A control unit, a battery, and an antenna are mounted on the circuit board. The circuit board has a length in a longitudinal direction and a length in a transverse direction and includes one or more copper-foil pattern layers. The antenna is disposed at one end in the longitudinal direction of the circuit board.

12 Claims, 9 Drawing Sheets

(51) Int. Cl.
  *H01Q 1/27*    (2006.01)
  *H01Q 9/30*    (2006.01)

(56)      References Cited

FOREIGN PATENT DOCUMENTS

| JP | 2004-167120 A | | 6/2004 |
|----|---------------|---|--------|
| JP | 2020014772 A | * | 1/2020 |
| WO | WO 2018/044959 A1 | | 3/2018 |
| WO | WO 2020/071925 A1 | | 4/2020 |

OTHER PUBLICATIONS

Search Report issued in European Application No. 22864375.5, dated May 16, 2025 (14 pages).
International Search Report in Application No. PCT/JP2022/ 031925, dated Oct. 25, 2022, 4 pages.

* cited by examiner

WIRED ANTENNA (METAL WIRE)
POWER SUPPLY LINE    11A    11

11D    +

11E

B↑                                    ↑B 11A-2                    11A-1

(B)    11

11B        11C        11E

HIGH
DIELECTRIC
MATERIAL

11D    + −

11A1

11A

6-LAYER
BOARD 11A-2                    11A-1

11B   11C        11A        11

11E

11D        GND

11A1

LIVING-BODY MONITORING DEVICE

CROSS-REFERENCE TO RELATED APPLICATIONS

This application is a 371 application of PCT/JP2022/031925 having an international filing date of Aug. 24, 2022, which claims priority to JP2021-142568 filed Sep. 1, 2021, the entire content of each of which is incorporated herein by reference.

TECHNICAL FIELD

The present invention relates to a living-body monitoring device.

Priority is claimed on Japanese Patent Application No. 2021-142568, filed Sep. 1, 2021, the content of which is incorporated herein by reference.

BACKGROUND ART

In the related art, an intraoral-installed living-body monitoring and treatment device is known (see Patent Document 1). In Patent Document 1, a living-body monitor built in a denture is described as an example of the intraoral-installed living-body monitoring and treatment device.

It is described in Patent Document 1 that data is transmitted to a management center such as a medical center in a wireless manner, but in the technique described in Patent Document 1, measures for efficiently radiating radio waves from the inside to the outside of an oral cavity are not taken, and thus there is concern of a large radio propagation loss due to radio wave absorption of the body tissue or the like. That is, with the technique described in Patent Document 1, radio waves cannot be efficiently radiated from the inside outside of the oral cavity when the intraoral-installed living body monitor is disposed in the oral cavity.

In the related art, a short-range radio communication signal coupler device for relaying monitoring data from an orthodontic monitoring device to a small processor is known (see Patent Document 2). An intraoral instrument, a monitoring device, and a communication unit transmitting sensor data to a remote device which are mounted in a patient's mouth are described in Patent Document 2.

In Patent Document 2, an antenna of the communication unit is mentioned, but placement of the antenna is not described. Depending on the placement of the antenna, a reader has to be inserted into the oral cavity to acquire measurement data in real time in a state in which a patient is wearing the intraoral living-body monitor, which is not practical.

CITATION LIST

Patent Document

Patent Document 1: Japanese Unexamined Patent Application, First Publication No. 2004-167120
Patent Document 2: United States Patent Application, Publication No. 2018/0000563

SUMMARY OF INVENTION

Technical Problem

In consideration of the aforementioned circumstances, an objective of the present invention is to provide a living-body monitoring device that can efficiently radiate radio waves from a living-body monitoring device provided in an oral cavity outside of the oral cavity.

Solution to Problem

According to an aspect of the present invention, there is provided a living-body monitoring device including: an electronic device including a circuit board; and a living-body wearing instrument fixing or sealing the electronic device, wherein a control unit, a battery, and an antenna are mounted on the circuit board, the circuit board has a length in a longitudinal direction and a length in a transverse direction and includes one or more copper-foil pattern layers, and the antenna is disposed at one end in the longitudinal direction of the circuit board.

With the living-body monitoring device according to the aspect of the present invention, since the circuit board having a length in the longitudinal direction and a length in the transverse direction and including the antenna is disposed at one end in the longitudinal direction of the circuit board, it is possible to efficiently radiate radio waves from the antenna of the living-body monitoring device disposed in the oral cavity outside of the oral cavity.

In the living-body monitoring device according to the aspect of the present invention, a sensor may be mounted on the circuit board, the living-body wearing instrument may be an intraoral instrument, and the living-body monitoring device may be disposed in an oral cavity such that the longitudinal direction of the circuit board is aligned with a row of teeth t.

In this case, since the circuit board is parallel to the row of teeth of the wearer when the living-body monitoring device is worn by the wearer, the wearer can wear the living-body monitoring device without feeling discomfort and it is possible to enhance wearability of the living-body monitoring device. That is, it is possible to enhance wearability of the living-body monitoring device and to efficiently radiate radio waves from the antenna of the living-body monitoring device disposed in the oral cavity outside of the oral cavity.

In the living-body monitoring device according to the aspect of the present invention, the intraoral instrument may be an orthodontic appliance, a denture, or an implant.

In this case, that is, when the intraoral instrument is an orthodontic appliance, a denture, or an implant, it is possible to feed biological information on dental treatment conditions detected by the sensor mounted on the circuit board of the living-body monitoring device back for treatment or treatment planning.

In the living-body monitoring device according to the aspect of the present invention, the intraoral instrument may be a mouthpiece orthodontic appliance that is mounted on crowns of one or more teeth and that covers part of gums of the one or more teeth.

In this case, that is, when the intraoral instrument is a mouthpiece orthodontic appliance, the circuit board is parallel to the row of teeth of the wearer when the living-body monitoring device is being worn by the wearer. Accordingly, similarly to when a general mouthpiece orthodontic appliance is being worn, the wearer can wear the living-body monitoring device without feeling discomfort and it is possible to minimize wearing discomfort of the living-body monitoring device.

In the living-body monitoring device according to the aspect of the present invention, the antenna may be a monopole antenna, the circuit board may include a first area which is an area in which the antenna is disposed and a second area which is an area other than the first area, and one or more copper-foil pattern layers out of the one or more copper-foil pattern layers disposed in the second area may be grounded.

In this case, that is, when the second area is grounded, a mirror image of the monopole antenna is formed and thus it is possible to enhance a radiation efficiency of the antenna. In this case, since the second area located at the other end in the longitudinal direction of the circuit board is grounded, it is possible to lengthen the grounding area, to increase a percentage of the area of a part contributing to generation of the mirror image to the whole area of the circuit board, and to maximize the radiation efficiency with the circuit board of a small size.

In the living-body monitoring device according to the aspect of the present invention, the monopole antenna may be a wired antenna that is formed on the circuit board.

In this case, when radio waves are radiated from the wired antenna formed on the circuit board, it is possible to decrease the size of the living-body monitoring device and to enhance a radiation efficiency of radio waves.

In the living-body monitoring device according to the aspect of the present invention, the monopole antenna may be a chip antenna including a high dielectric material.

In this case, when the monopole antenna is a chip antenna including a high dielectric material, it is possible to decrease the size of the living-body monitoring device.

In the living-body monitoring device according to the aspect of the present invention, the monopole antenna may be formed by combining a wired antenna formed on the circuit board and a chip antenna including a high dielectric material.

In the living-body monitoring device according to the aspect of the present invention, the battery may be disposed on a side opposite to the antenna with the control unit interposed therebetween.

In this case, it is possible to decrease the size in the transverse direction of the circuit board without damaging wearability of the living-body monitoring device and to enhance a radiation efficiency of radio waves from the antenna.

In the living-body monitoring device according to the aspect of the present invention, the circuit board may include a long side and a short side, and a ratio between the long side and the short side may be equal to or greater than 2.

In this case, it is possible to enhance a radiation efficiency of radio waves from the antenna to 20% or more of maximum efficiency.

When a wearer wears the living-body monitoring device such that the circuit board is parallel to the row of teeth, it was found through intensive study by the inventors that the wearer may feel discomfort at the time of wearing the living-body monitoring device when the short side of the circuit board is greater than about 15 mm which is a length from the "gum-cheek transition region to the dental cusp" (from the bottom of the gum to the top of a tooth) of a regular adult.

Therefore, in the living-body monitoring device according to the aspect of the present invention, the short side may be less than 15 mm.

In this case, it is possible to curb concern about the wearer's feeling discomfort at the time of wearing the living-body monitoring device.

In the living-body monitoring device according to the aspect of the present invention, the long side may be less than 30 mm.

In this case, it is possible to curb concern about a wearer feeling discomfort at the time of wearing the living-body monitoring device.

In the living-body monitoring device according to the aspect of the present invention, the ratio between the long side and the short side may be equal to or greater than 3.5 and equal to or less than 7.

In this case, it is possible to secure a radiation efficiency of radio waves from the antenna to 60% or more of the maximum efficiency.

In the living-body monitoring device according to the aspect of the present invention, the control unit may set a first radiated radio wave intensity which is an intensity of radio waves radiated from the antenna when the living-body monitoring device is disposed inside of the oral cavity and a second radiated radio wave intensity which is an intensity of radio waves radiated from the antenna when the living-body monitoring device is disposed outside of the oral cavity to be different, and a ratio of the second radiated radio wave intensity to the first radiated radio wave intensity may be equal to or greater than 0.1 and equal to or less than 0.2.

In this case, a received signal intensity of radio waves radiated from the antenna when the living-body monitoring device is disposed inside of the oral cavity and a received signal intensity of radio waves radiated from the antenna when the living-body monitoring device is disposed outside of the oral cavity can be made substantially to be the same.

That is, in this case, design is performed with a weight given to a radio wave intensity when the living-body monitoring device is disposed inside of the oral cavity in consideration of a loss (about-8 dB) when radio waves are radiated from the antenna of the living-body monitoring device disposed inside of the oral cavity outside of the oral cavity.

In the living-body monitoring device according to the aspect of the present invention, the antenna may be located on a lip side in the oral cavity when the living-body monitoring device is disposed in the oral cavity.

In this case, it is possible to decrease a distance from the antenna to the outside (the outside of the oral cavity) and to radiate radio waves to the outside of the oral cavity by curbing radio wave absorption by a human body (a wearer of the living-body monitoring device). Accordingly, it is possible to curb consumption of the battery and to minimize radio wave absorption by the human body.

In the living-body monitoring device according to the aspect of the present invention, a main lobe of a radiation pattern of the antenna may be directed outside of the oral cavity via the lips.

In this case, it is possible to provide appropriate radiation directivity and to efficiently radiate radio waves from the antenna of the living-body monitoring device disposed in the oral cavity outside of the oral cavity.

In the living-body monitoring device according to the aspect of the present invention, the living-body monitoring device may be disposed on a palate side in the oral cavity for use.

In this case, it is possible to avoid radio wave absorption by the gum and the cheek of the wearer of the living-body monitoring device and to efficiently radiate radio waves from the antenna of the living-body monitoring device disposed in the oral cavity outside of the oral cavity.

In the living-body monitoring device according to the aspect of the present invention, a sensor may be mounted on the circuit board, the living-body wearing instrument may be an intraoral instrument, the sensor may detect an open/closed state of the lips of a wearer of the living-body monitoring device, and the control unit may switch a communication status according to the open/closed state of the lips of the wearer of the living-body monitoring device detected by the sensor.

In this case, that is, when the communication status is switched according to the open/closed state of the lips of the wearer of the living-body monitoring device (for example, when an interval, electric power consumption, or an information type of communication is switched), it is possible to efficiently transmit data, for example, by transmitting data mainly when the lips of the wearer are in the open state in which communication can be easily performed and curbing communication when the lips of the wearer are in the closed state in which a loss is large.

In the living-body monitoring device according to the aspect of the present invention, a sensor may be mounted on the circuit board, the living-body wearing instrument may be an intraoral instrument, the sensor may detect an open/closed state of the lips of a wearer of the living-body monitoring device, and the control unit may radiate radio waves from the antenna when the open state of the lips of the wearer of the living-body monitoring device is detected by the sensor.

In this case, that is, when the lips of the wearer of the living-body monitoring device are in the open state and radio waves are radiated from the antenna of the living-body monitoring device disposed in the oral cavity of the wearer, it is possible to curb useless radiation of radio waves (that is, radiation of radio waves from the antenna of the living-body monitoring device disposed in the oral cavity of the wearer when the lips of the wearer are in the closed state) and to efficiently radiate radio waves from the antenna of the living-body monitoring device disposed in the oral cavity outside of the oral cavity.

Advantageous Effects of Invention

According to the present invention, it is possible to provide a living-body monitoring device that can efficiently radiate radio waves from the living-body monitoring device provided in an oral cavity outside of the oral cavity.

BRIEF DESCRIPTION OF DRAWINGS

FIG. 5 is a diagram illustrating an example of a relationship between an external device performing radio communication with the living-body monitoring device and the living-body monitoring device.

DESCRIPTION OF EMBODIMENT

Hereinafter, a living-body monitoring device according to an embodiment of the present invention will be described with reference to the accompanying drawings.

First Embodiment

Figure 1:
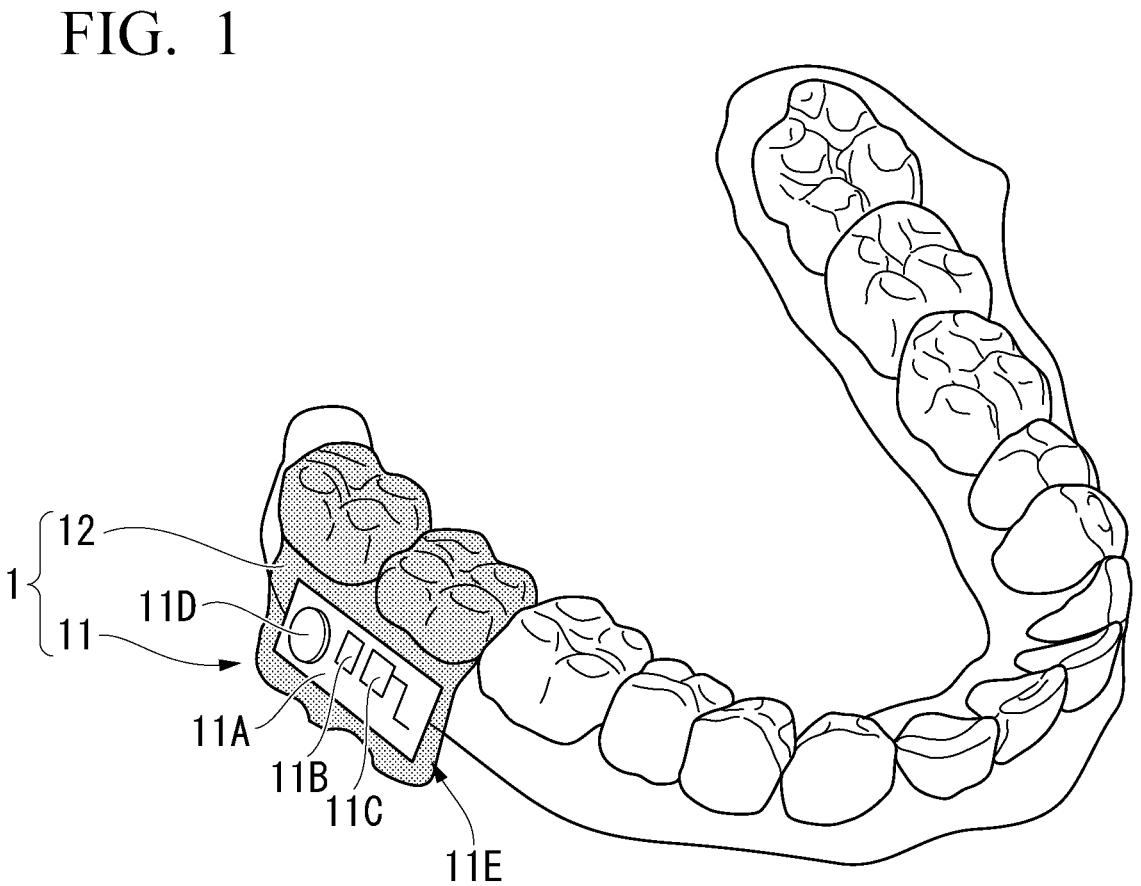
FIG. 1 is a diagram illustrating an example of a living-body monitoring device according to a first embodiment.
Figure 2:
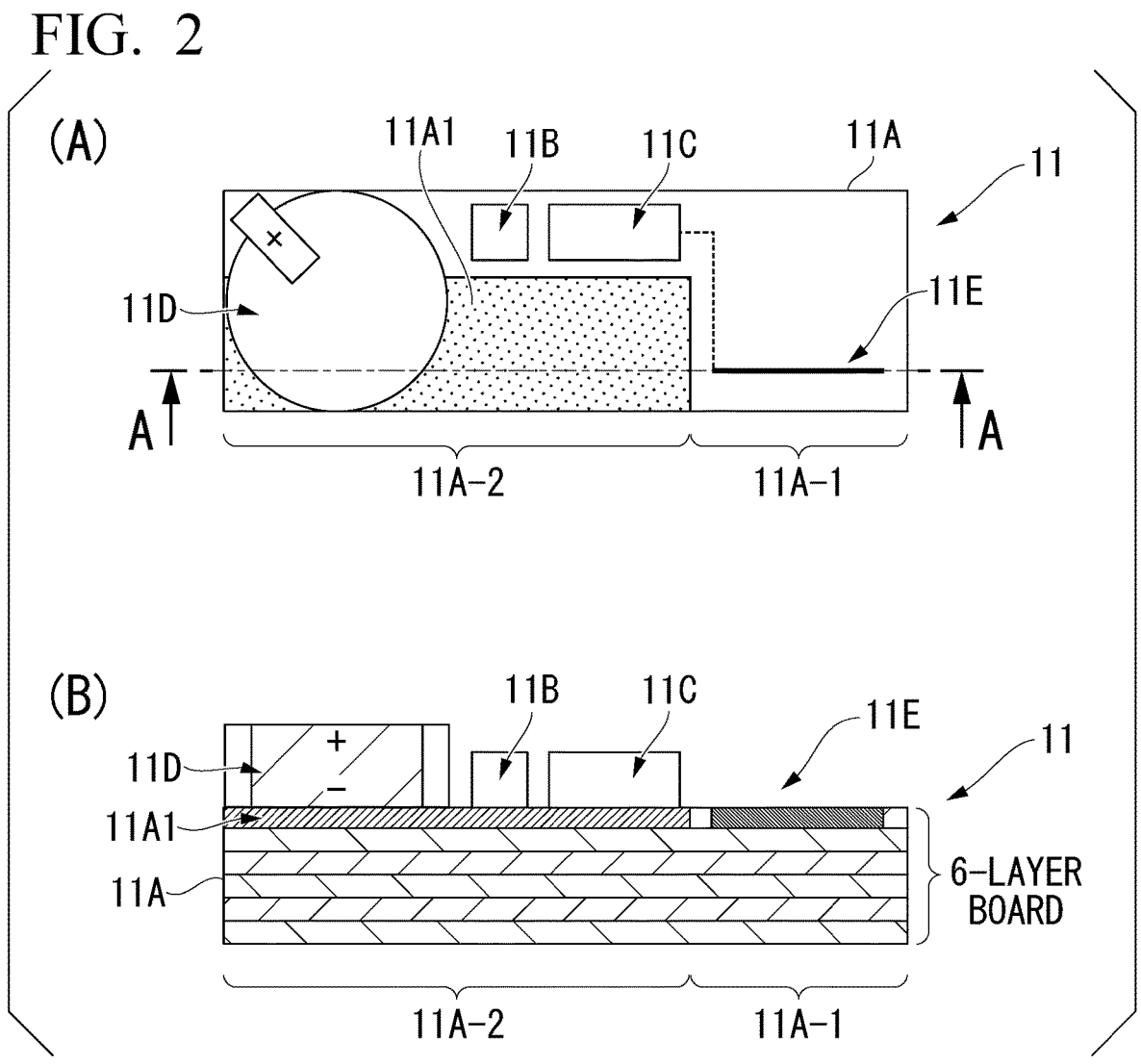
FIG. 2 is a diagram illustrating an example of an electronic device constituting part of the living-body monitoring device.
Figure 3:
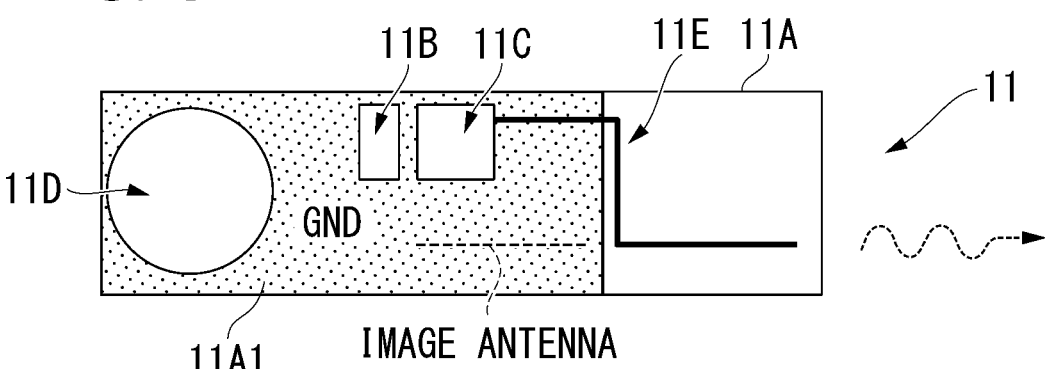
FIG. 3 is a diagram illustrating an example of a mirror image of an antenna of the electronic device which is formed in the electronic device.

FIG. 1 is a diagram illustrating an example of a living-body monitoring device 1 according to a first embodiment. Specifically, FIG. 1 illustrates a state in which the living-body monitoring device 1 is being worn by a wearer of the living-body monitoring device 1. FIG. 2 is a diagram illustrating an example of an electronic device 11 constituting part of the living-body monitoring device 1. FIG. 2(A) is a plan view of the electronic device 11, and FIG. 2(B) is a sectional view taken along line A-A in FIG. 2(A). FIG. 3 is a diagram illustrating an example of a mirror image of an antenna 11E of the electronic device 11 which is formed in the electronic device 11.

In the example illustrated in FIGS. 1 to 3, the living-body monitoring device 1 includes an electronic device 11 and a living-body wearing instrument 12. The electronic device 11 includes a circuit board 11A. The circuit board 11A is a 6-layer board including a copper-foil pattern layer 11A1 (see FIG. 2(B)).

For example, the circuit board 11A may be a board including layers other than 6 layers.

In the example illustrated in FIG. 2(B), the circuit board 11A includes a single copper-foil pattern layer 11A1. For example, the circuit board 11A may include a plurality of copper-foil pattern layers.

In the example illustrated in FIGS. 1 to 3, a sensor 11B, a control unit 11C, a battery 11D, and an antenna 11E are mounted on the circuit board 11A.

The sensor 11B is at least one of an optical sensor (for example, a pulse wave sensor, a pulse oximeter, or a glucose sensor), a strain sensor, an acceleration sensor, a gyro sensor, and a temperature sensor described in Japanese Unexamined Patent Application, First Publication No. 2020-014773 and Japanese Unexamined Patent Application, First Publication No. 2020-141789 and detects biological information (specifically, biological information of a wearer of the living-body monitoring device 1).

The control unit 11C performs a process of converting the biological information detected by the sensor 11B to a high-frequency signal. The control unit 11C has a function of a radio communication unit and a function of a signal processing unit. The battery 11D supplies electric power to the sensor 11B, the control unit 11C, and the like. The battery 11D is placed on the side opposite to the antenna 11E with the control unit 11C interposed therebetween. This is for preventing radio waves radiated from the antenna 11E from being absorbed by a metal tube of the battery 11D. The antenna 11E also has a function of receiving radio waves transmitted form an external device 2 (see FIG. 5) in addition to the function of radiating radio waves.

The circuit board 11A includes a long side and a short side. That is, the circuit board 11A has a length in a longitudinal direction (a right-left direction in FIG. 2(A)) and a length in a transverse direction (an up-down direction in FIG. 2(A)). A ratio between the long side and the short side is equal to or greater than 2. Specifically, the short side is less than 15 mm, and the long side is less than 30 mm. The ratio between the long side and the short side (long side/short side) is equal to or greater than 3.5 and equal to or less than 7. Accordingly, it is possible to enhance the radiation efficiency of radio waves from the living-body monitoring device 1 to 60% or higher.

When the short side of the circuit board 11A is greater than about 15 mm which is a length from the "gum-cheek transition region to the dental cusp" (from the bottom of the gum to the top of a tooth) of a regular adult, a wearer of the living-body monitoring device 1 may feel discomfort at the time of wearing the living-body monitoring device 1 such that it is parallel to the row of teeth, and thus the short side of the circuit board 11A is set to be less than 15 mm as described above.

Figure 4:
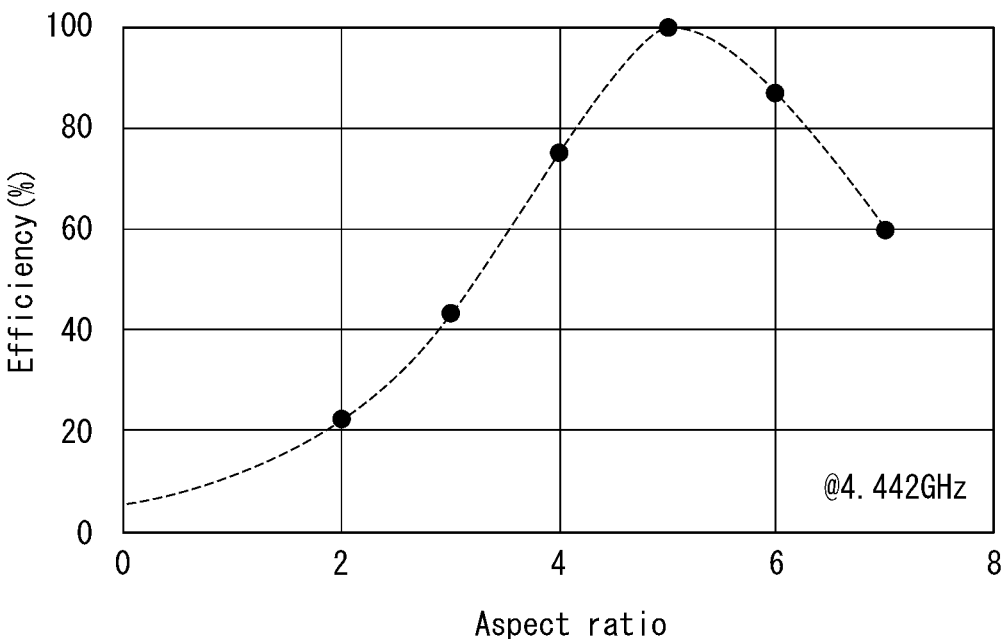
FIG. 4 is a diagram illustrating an example of a relationship between a ratio between a long side and a short side of a circuit board and the radiation efficiency of radio waves from the circuit board.

FIG. 4 is a diagram illustrating an example of a relationship between the ratio between the long side and the short side of the circuit board 11A and a radiation efficiency of radio waves from the circuit board 11A. Specifically, the horizontal axis of FIG. 4 represents the ratio between the long side and the short side of the circuit board 11A, and the vertical axis of FIG. 4 represents the radiation efficiency of radio waves from the circuit board 11A (relative efficiency when the maximum efficiency is 100%). In the example illustrated in FIG. 4, the frequency of radio waves radiated from the circuit board 11A is 4.442 GHz.

When a radiation efficiency of radio waves of 20% (−7 dB) is allowed, the ratio has to be equal to or greater than 2. The radio wave radiation efficiency of 20% means that only electric power of −7 dBm can be used for radiation of radio waves in spite of ignoring of losses in the power supply line and the antenna 1E when transmission electric power of 0 dBm is supplied from the radio communication unit (the control unit 11C) to the antenna 1E. Since radiated radio waves are further attenuated by the body tissue or a free propagation loss, the radio wave radiation efficiency of 20% is minimum efficiency required for the external device 2 (see FIG. 5) to receive the radio waves.

In the example illustrated in FIGS. 1 to 3, the ratio between the long side and the short side of the circuit board 11A is set to be equal to or greater than 3.5 and equal to or less than 7 on the basis of the relationship between the ratio between the long side and the short side of the circuit board 11A and the radiation efficiency of radio waves from the circuit board 11A which is illustrated in FIG. 4.

In the example illustrated in FIGS. 1 to 3, the circuit board 11A has a rectangular shape. For example, the circuit board 11A may have a shape (for example, a shape in which four corners of a rectangle are chamfered in an arc shape) other than the rectangular shape. That is, the circuit board 11A may not have a short side (a linear short side).

In the example illustrated in FIGS. 1 to 3, the antenna 11E is disposed at one end in the longitudinal direction (the right end in FIG. 2(A)) of the circuit board 11A and is a monopole antenna. This is for preventing another component mounted on the circuit board 11A from being present in a propagation path of radio waves radiated from the antenna 11E. By disposing the antenna 11E at one end in the longitudinal direction of the circuit board 11A, it is possible to minimize an influence of the other component mounted on the circuit board 11A on radiation of radio waves and to radiate radio waves from an end of the circuit board 11A.

The circuit board 11A includes a first area 11A-1 which is an area in which the antenna 11E is disposed and a second area 11A-2 which is an area other than the first area 11A-1. Specifically, as illustrated in FIG. 2(B), the copper-foil pattern layer 11A1 provided in the second area 11A-2 is grounded.

For example, a plurality of copper-foil patterns may be disposed in the second area 11A-2, and one or more copper-foil pattern layers out of the plurality of copper-foil patterns disposed in the second area 11A-2 may be grounded.

In the example illustrated in FIGS. 1 to 3, the monopole antenna (the antenna 11E) is a wired antenna formed on the circuit board 11A. Since the copper-foil pattern layer 11A1 disposed in the second area 11A-2 is grounded as described above, a mirror image (illustrated as an "image antenna" in FIG. 3) of the monopole antenna (the antenna 11E) is formed in the second area 11A-2, as illustrated in FIG. 3. As a result, the monopole antenna virtually operates as a dipole antenna and thus it is possible to enhance a radiation efficiency of the antenna (that is, both the antenna 11E and the image antenna).

As illustrated in FIGS. 2(A) and 2(B), the grounded copper-foil pattern layer 11A1 is disposed in the second area 11A-2 in which the antenna 11E is not provided. Accordingly, it is possible to increase the size in the longitudinal direction (the size in the right-left direction in FIGS. 2(A) and 2(B)) of the grounding area (that is, an area with the ground potential). As a result, it is possible to increase the percentage of the area of a part contributing to generation of a mirror image to the total area of the circuit board 11A and to maximize the radiation efficiency of the circuit board 11A with a minimal size.

In the example illustrated in FIGS. 1 to 3, the living-body wearing instrument 12 seals the electronic device 11. That is, the electronic device 11 is embedded in the living-body wearing instrument 12. For example, the living-body wearing instrument 12 may fix the electronic device 11 instead of sealing the electronic device 11.

It is preferable that the living-body monitoring device 1 have a shape which is as small as possible and which does not gives discomfort at the time of wearing in order not to damage wearability of a wearer of the living-body monitoring device 1. When the living-body monitoring device 1 is attached to a location (a side surface of a crown) other than a fitting surface of the crown such that dental occlusion is not badly affected, there is concern that teeth gums, and other body tissue may contact or interfere with the living-body monitoring device 1 at the time of fitting to badly affect the fitting and to damage wearability when the circuit board 11A is long in the height direction of the teeth.

On the other hand, in a direction parallel to an occlusion plane (a direction aligned with the row of teeth), the length of the circuit board 11A is allowed to a certain extent. There is no particular discomfort when the number of teeth corresponding to the length is two or three, and bad affection on the fitting function can be prevented by making the circuit board 11A flexible even if the number of teeth corresponding to the length is more. The circuit board 11A mentioned herein may be, for example, a rigid board formed of flame retardant (FR)-4, a flexible board formed of polyimide, or a rigid flexible board which is a combination thereof.

In the example illustrated in FIGS. 1 to 3, the living-body wearing instrument 12 is an intraoral instrument. Specifically, the living-body monitoring device 1 is disposed in the oral cavity by the living-body wearing instrument 12 (the intraoral instrument) such that the longitudinal direction (the right-left direction in FIGS. 2(A) and 2(B)) of the circuit board 11A is aligned with the row of teeth as illustrated in FIG. 1. When the living-body monitoring device 1 is disposed in the oral cavity as illustrated in FIG. 1, the antenna 11E is located in part of the living-body monitoring device 1 on the lip side in the oral cavity (on the lower-right side in FIG. 1).

In the example illustrated in FIGS. 1 to 3, the living-body wearing instrument 12 (the intraoral instrument) is a mouthpiece orthodontic appliance that is attached to crowns of one or more teeth and covers part of the gums of the one or more teeth.

For example, the living-body wearing instrument 12 (the intraoral instrument) may be an orthodontic appliance, a denture, or an implant.

Figure 5:
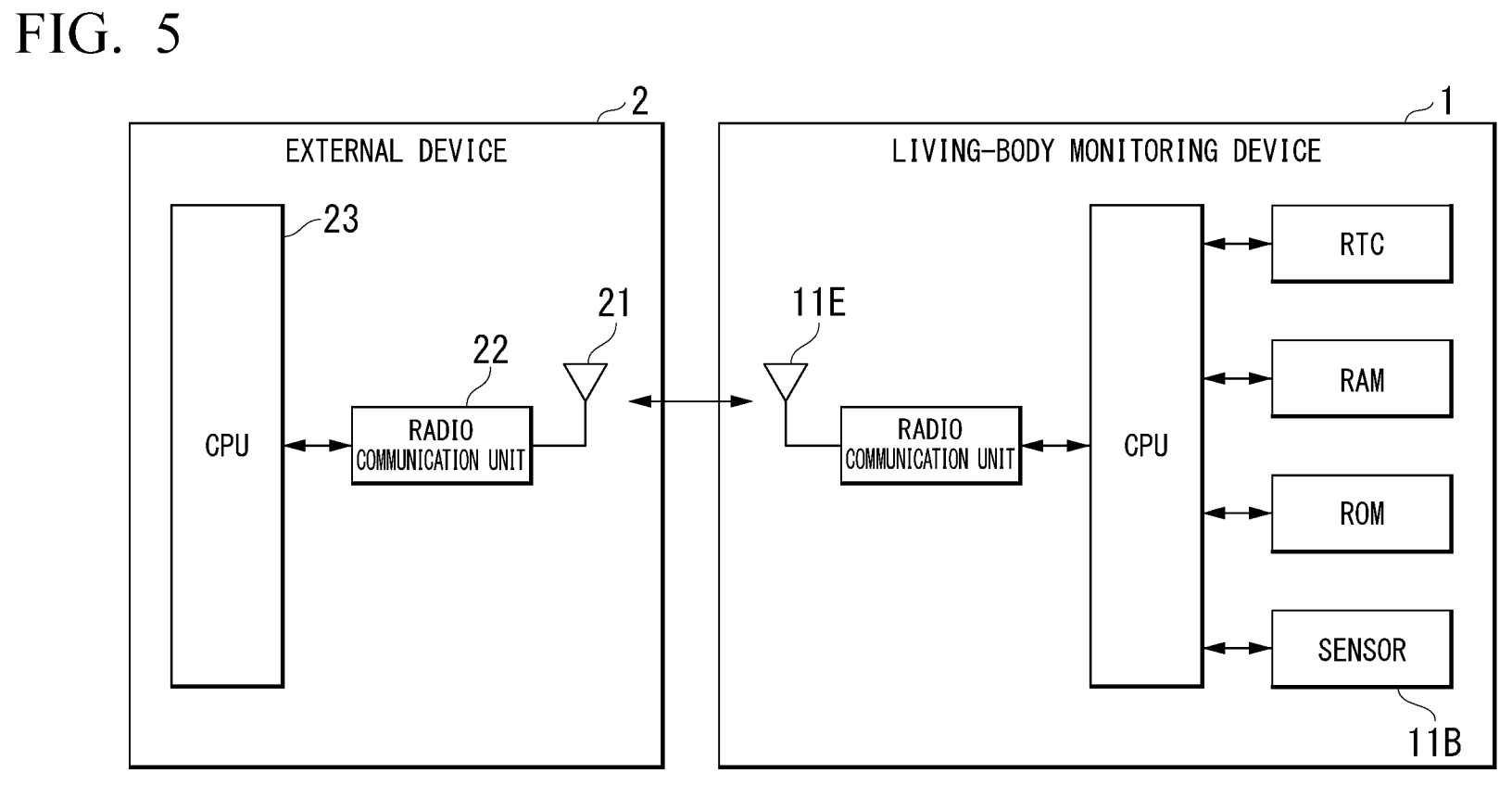

FIG. 5 is a diagram illustrating an example of a relationship between an external device 2 performing radio communication with the living-body monitoring device 1 and the living-body monitoring device 1.

In the example illustrated in FIG. 5, the living-body monitoring device 1 disposed inside of the oral cavity of a wearer performs radio communication with an external device 2 disposed outside of the oral cavity of the wearer. A "radio communication unit," a "central processing unit (CPU)," a "real-time clock (RTC)," a "random access memory (RAM)," and a "read only memory (ROM)" of the living-body monitoring device 1 illustrated in FIG. 5 correspond to the control unit 11C illustrated in FIGS. 1 to 3. The external device 2 includes an antenna 21, a radio communication unit 22, and a CPU 23.

Biological information of the wearer of the living-body monitoring device 1 detected by the sensor 11B of the living-body monitoring device 1 is converted to a high-frequency signal indicating the biological information of the wearer by the CPU and the radio communication unit. The antenna 11E of the living-body monitoring device 1 transmits radio waves indicating the biological information of the wearer, and the antenna 21 of the external device 2 receives radio waves transmitted from the antenna 11E of the living-body monitoring device 1. The radio communication unit 22 and the CPU 23 of the external device 2 demodulates the biological information of the wearer of the living-body monitoring device 1 included in the radio waves received by the antenna 21. A radio communication system between the living-body monitoring device 1 and the external device 2 can employ, for example, a known radio communication system such as Bluetooth (registered trademark), Bluetooth Low Energy, WiFi, or Low Power Wide Area (LPWA).

When communication is performed from the antenna 11E of the living-body monitoring device 1 disposed inside of the oral cavity of the wearer of the living-body monitoring device 1 to the external device 2 disposed outside of the oral cavity of the wearer, most radio waves radiated from the antenna 11E are absorbed by the body tissue in the vicinity of the antenna 11E or in the propagation path. Accordingly, it is important to appropriately arrange the antenna 11E and the like and to provide sufficient directivity such that the living-body monitoring device 1 efficiently radiates radio waves outside of the oral cavity of the wearer.

Figure 6:
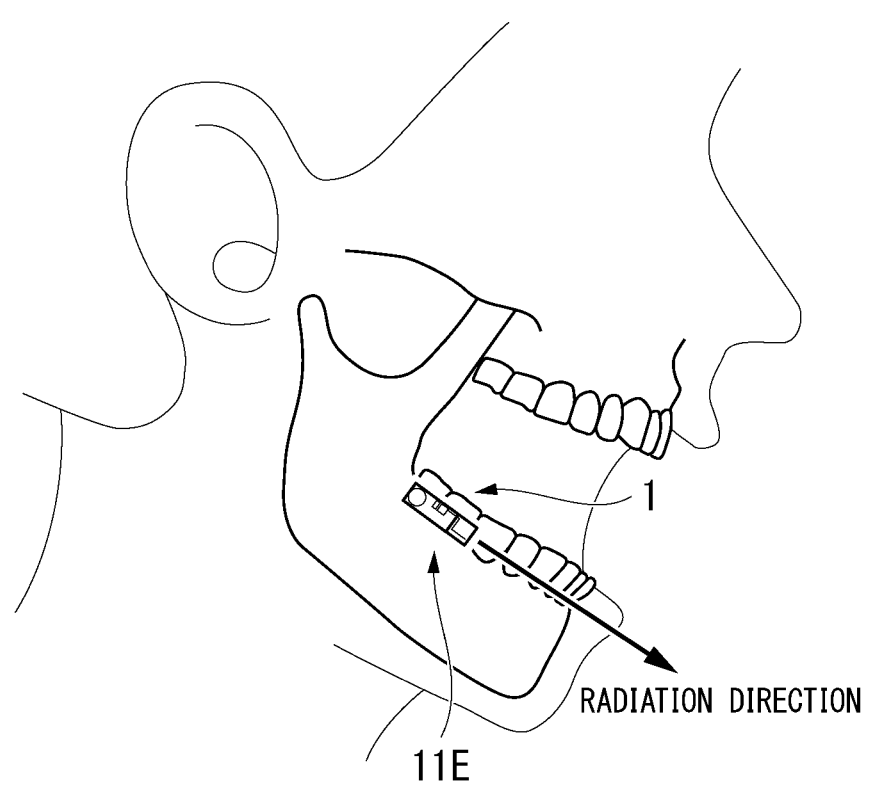
FIG. 6 is a diagram illustrating an example of a radiation direction of radio waves from an antenna of the living-body monitoring device which is worn in an oral cavity of a wearer.
Figure 7:
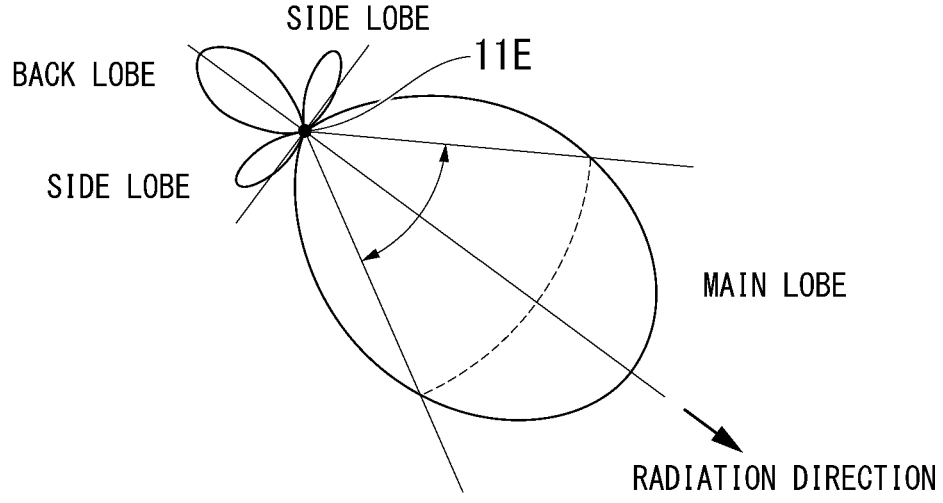
FIG. 7 is a diagram illustrating an example of a radiation pattern of the antenna of the living-body monitoring device.

FIG. 6 is a diagram illustrating an example of a radiation direction of radio waves from the antenna 11E of the living-body monitoring device 1 which is being worn in the oral cavity of a wearer. FIG. 7 is a diagram illustrating an example of a radiation pattern of the antenna 11E of the living-body monitoring device 1.

In the example illustrated in FIGS. 6 and 7, when the living-body monitoring device 1 is disposed in the oral cavity of the wearer, the antenna 11E is located in part of the living-body monitoring device 1 on the lip side in the oral cavity (on the lower-right side in FIG. 6), and a main lobe of the radiation pattern of the antenna 11E is directed outside of the oral cavity via the lips. That is, the main lobe of the radiation pattern of the antenna 11E illustrated in FIG. 7 is disposed on an arrow indicating the "radiation direction" in FIG. 6.

When communication to the external device 2 disposed outside of the oral cavity is performed, a propagation path is shortened with this arrangement and thus an intensity of radio waves absorbed by the human body is decreased, thereby curbing attention of radio waves. Since radio wave absorption by the body tissue is also curbed, it is possible to decrease a likelihood of damage in health. Most of electric power supplied to the antenna 11E can be made to contribute to radiation of radio waves.

The radiation direction of the main lobe is affected by an installation direction of the antenna 11E and shapes and arrangement of components mounted on the circuit board 11A and other constituent components of the living-body monitoring device 1. Accordingly, it is preferable that the main lobe be designed to be directed outside of the oral cavity by adjusting such factors.

In a device that can be attached to and detached from the oral cavity at an arbitrary timing, a maximum propagation distance when the device is installed inside of the oral cavity and a maximum propagation distance when the device is installed outside of the oral cavity have only to be equal in general. For example, in a device that communicates with an external device such as a smartphone, a distance from the device installed inside of the oral cavity of a user to the external device and a distance from the device disposed outside of the oral cavity to the external device are not much different in general (it is assumed that the device is detached and placed near the user). Accordingly, by setting the ratio of the radiated radio wave intensity when the device is installed outside of the oral cavity to the radiated radio wave intensity when the device is installed inside of the oral cavity to range from 0.1 times to 0.2 times in consideration of a propagation loss (about −8 dB=0.15) when radio waves are radiated from the inside outside of the oral cavity, radio wave radiation characteristics thereof can be made to be equal even if the device is placed in any of the inside and the outside of the oral cavity. For this purpose, it is preferable that design be performed with a weight given to the radio wave intensity when the device is installed inside of the oral cavity, and, for example, it is conceivable that design be performed such that matching in the inside of the oral cavity be achieved, that is, a voltage standing wave ratio (VSWR) in the oral cavity be lowered by performing matching of the antenna in an environment imitating the oral cavity. Accordingly, since the maximum propagation distance to the outside of the oral cavity is decreased, but the maximum propagation distance of radio waves radiated from the inside of the oral cavity is increased, the total maximum propagation distance (that is, the maximum propagation distance at the time of use in the inside and the outside of the oral cavity) is improved.

In the example illustrated in FIGS. 1 to 7, the sensor 11B detects information indicating whether the living-body monitoring device 1 is disposed inside of the oral cavity of the wearer or outside of the oral cavity of the wearer (for example, detects a pulse wave and a temperature of the wearer of the living-body monitoring device 1) in consideration of the aforementioned description.

The control unit 11C sets a first radiated radio wave intensity which is an intensity of radio waves radiated from the antenna 11E when the sensor 11B detects that the living-body monitoring device 1 is disposed inside of the oral cavity and a second radiated radio wave intensity which is an intensity of radio waves radiated from the antenna 11E when the sensor 11B detects that the living-body monitoring device 1 is disposed outside of the oral cavity of the wearer to be different. Specifically, the control unit 11C sets the ratio of the second radiated radio wave intensity to the first radiated radio wave intensity to be equal to or greater than 0.1 and equal to or less than 0.2. That is, the control unit 11C sets radio waves radiated from the antenna 11E when the living-body monitoring device 1 is disposed inside of the oral cavity of the wearer to be more intense than radio waves radiated from the antenna 11E when the living-body monitoring device 1 is disposed outside of the oral cavity of the wearer.

As a result, the intensity of radio waves received by the antenna 21 of the external device 2 when the living-body monitoring device 1 is disposed inside of the oral cavity of the wearer and the intensity of radio waves received by the antenna 21 of the external device 2 when the living-body monitoring device 1 is disposed outside of the oral cavity of the wearer can be made to be substantially equal.

In the example illustrated in FIGS. 1 to 7, the living-body monitoring device 1 includes the sensor 11B. For example, the living-body monitoring device 1 may not include the sensor 11B. In this example, the living-body monitoring device 1 serves as a relay device that relays biological information.

Second Embodiment

A living-body monitoring device according to a second embodiment of the present invention will be described below.

The living-body monitoring device 1 according to the second embodiment has the same configuration as the living-body monitoring device 1 according to the first embodiment except the following description. Accordingly, with the living-body monitoring device 1 according to the second embodiment, it is possible to achieve the same advantages as with the living-body monitoring device 1 according to the first embodiment.

As described above, the sensor 11B in the living-body monitoring device 1 according to the first embodiment has a function of detecting biological information of a wearer of the living-body monitoring device 1.

In the living-body monitoring device 1 according to the second embodiment, the sensor 11B has a function of detecting biological information of the wearer of the living-body monitoring device 1 and a function of detecting an open/closed state of the lips of the wearer of the living-body monitoring device 1.

In the living-body monitoring device 1 according to the second embodiment, the control unit 11C switches a communication status according to the open/closed state of the lips of the wearer of the living-body monitoring device 1 detected by the sensor 11B. In communication from the inside of the oral cavity to the outside of the oral cavity, this is because the propagation loss to the external device 2 is small when the lips of the wearer of the living-body monitoring device 1 are in the open state, and radio wave absorption by the body tissue is remarkable and thus the propagation loss increases when the lips is in the closed state.

The communication status mentioned herein includes an interval at which communication is performed, an amount of electric power supplied to the antenna 11E, and an amount of information. That is, communication is performed with a shot interval, a small amount of electric power, and a large amount of information in the open state of the lips of the wearer of the living-body monitoring device 1 in which an S/N is high and a loss is small, and communication is performed with a long interval, a large amount of electric power, and a small amount of information in the closed state of the lips of the wearer of the living-body monitoring device 1 in which the S/N is low and the loss is large, By employing this configuration, it is possible to curb communication in the closed state of the lips of the wearer of the living-body monitoring device 1 in which a large amount of electric power supplied to the antenna 11E is required and to perform communication with low power consumption mainly in the open state of the lips of the wearer of the living-body monitoring device 1.

As the sensor 11B for detecting the open/closed state of the lips of the wearer of the living-body monitoring device 1, for example, an optical sensor (which senses brightness in the open state of the lips of the wearer of the living-body monitoring device 1), a thermal sensor (which senses an air flow in the open state of the lips of the wearer of the living-body monitoring device 1), a pressure sensor (which senses that fitting between teeth is weakened in the open state of the lips of the wearer of the living-body monitoring device 1), an acceleration sensor (which senses acceleration of an opening/closing motion of the lips of the wearer of the living-body monitoring device 1), or a gyro sensor (which senses a slope of the chin based on the opening/closing motion of the lips of the wearer of the living-body monitoring device 1) can be used, and a combination thereof may be used.

Figure 8:
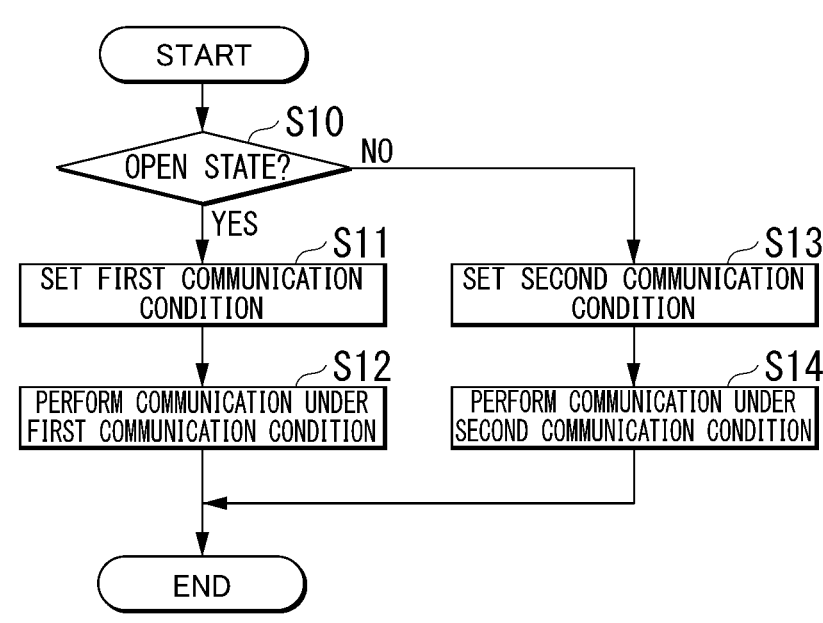
FIG. 8 is a flowchart illustrating an example of a process flow which is performed by a living-body monitoring device according to a second embodiment.

FIG. 8 is a flowchart illustrating an example of a process flow which is performed by the living-body monitoring device 1 according to the second embodiment.

In the example illustrated in FIG. 8, in Step S10, for example, the control unit 11C determines whether the lips of the wearer of the living-body monitoring device 1 is in the open state on the basis of the open/closed state of the lips of the wearer of the living-body monitoring device 1 detected by the sensor 11B. The process flow proceeds to Step S11 when the lips of the wearer of the living-body monitoring device 1 is in the open state, and the process flow proceeds to Step S13 when the lips of the wearer of the living-body monitoring device 1 is not in the open state.

In Step S11, for example, the control unit 11C sets the communication condition of the living-body monitoring device 1 to a first communication condition which is a communication condition for a high S/N propagation path.

Specifically, for example, the control unit 11C increases the communication frequency of the living-body monitoring device 1, decreases an amount of transmission electric power of the living-body monitoring device 1, and increases an amount of information transmitted and received by the living-body monitoring device 1.

Subsequently, in Step S12, the control unit 11C performs communication under the first communication condition (that is, the antenna 11E radiates radio waves under the first communication condition).

In Step S13, for example, the control unit 11C sets the communication condition of the living-body monitoring device 1 to a second communication condition which is a communication condition for a low S/N propagation path. Specifically, for example, the control unit 11C decreases the communication frequency of the living-body monitoring device 1, increases an amount of transmission electric power of the living-body monitoring device 1, and decreases an amount of information transmitted and received by the living-body monitoring device 1.

Subsequently, in Step S14, the control unit 11C performs communication under the second communication condition (that is, the antenna 11E radiates radio waves under the second communication condition).

Third Embodiment

A living-body monitoring device according to a third embodiment of the present invention will be described below.

The living-body monitoring device 1 according to the third embodiment has the same configuration as the living-body monitoring device 1 according to the second embodiment except the following description. Accordingly, with the living-body monitoring device 1 according to the third embodiment, it is possible to achieve the same advantages as with the living-body monitoring device 1 according to the second embodiment except the following description.

As described above, in the living-body monitoring device 1 according to the second embodiment, the control unit 11C performs communication under the second communication condition (that is, the antenna 11E radiates radio waves under the second communication condition) when the lips of the wearer of the living-body monitoring device 1 are not in the open state (are in the closed state).

In the living-body monitoring device 1 according to the third embodiment, the control unit 11C does not perform communication with the external device 2 when the lips of the wearer of the living-body monitoring device 1 are not in the open state (are in the closed state).

In the living-body monitoring device 1 according to the third embodiment, the control unit 11C radiates radio waves from the antenna 11E when the lips of the wearer of the living-body monitoring device 1 are in the open state (that is, when the sensor 11B detects the open state of the lips of the wearer of the living-body monitoring device 1).

For example, the usage in which a small amount of information is transmitted to the external device 2 can be performed separately by performing advertisement of Bluetooth Low Energy when the lips of the wearer of the living-body monitoring device 1 are in the open state.

When the closed state of the lips of the wearer of the living-body monitoring device 1 is maintained for a long time, or the like, the antenna 11E may be supplied with a large amount of electric power to perform communication as needed in order to transmit information to the external device 2.

Figure 9:
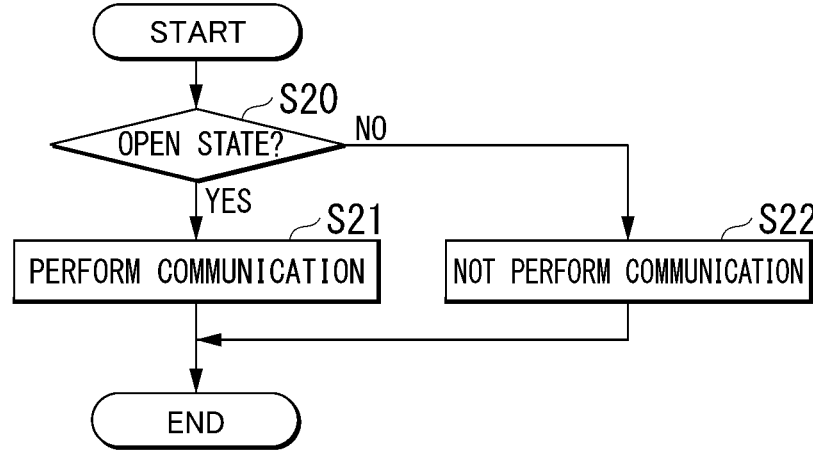
FIG. 9 is a flowchart illustrating an example of a process flow which is performed by a living-body monitoring device according to a third embodiment.

FIG. 9 is a flowchart illustrating an example of a process flow which is performed by the living-body monitoring device 1 according to the third embodiment.

In the example illustrated in FIG. 9, in Step S20, for example, the control unit 11C determines whether the lips of the wearer of the living-body monitoring device 1 is in the open state on the basis of the open/closed state of the lips of the wearer of the living-body monitoring device 1 detected by the sensor 11B. The process flow proceeds to Step S21 when the lips of the wearer of the living-body monitoring device 1 is in the open state, and the process flow proceeds to Step S22 when the lips of the wearer of the living-body monitoring device 1 is not in the open state.

In Step S21, the control unit 11C performs communication with the external device 2 (that is, the living-body monitoring device 1 transmits biological information of the wearer of the living-body monitoring device 1 detected by the sensor 11B to the external device 2).

On the other hand, in Step S22, the control unit 11C does not perform communication with the external device 2 (that is, the living-body monitoring device 1 does not transmit biological information of the wearer of the living-body monitoring device 1 detected by the sensor 11B to the external device 2).

Fourth Embodiment

A living-body monitoring device according to a fourth embodiment of the present invention will be described below.

The living-body monitoring device 1 according to the fourth embodiment has the same configuration as the living-body monitoring device 1 according to the first embodiment except the following description. Accordingly, with the living-body monitoring device 1 according to the fourth embodiment, it is possible to achieve the same advantages as with the living-body monitoring device 1 according to the first embodiment except the following description.

As illustrated in FIGS. 1 and 6, the living-body monitoring device 1 according to the first embodiment is disposed at a position between a molar and a gum-cheek of the wearer in the oral cavity of the wearer of the living-body monitoring device 1 for use.

On the other hand, the living-body monitoring device 1 according to the fourth embodiment is disposed on a palate side (at a position behind the upper front tooth of the wearer) in the oral cavity of the wearer of the living-body monitoring device 1 for use. Accordingly, it is possible to curb concern about absorption of radio waves radiated from the antenna 11E of the living-body monitoring device 1 by the gum-cheek of the wearer and to efficiently radiate radio waves from the antenna 11E of the living-body monitoring device 1 outside of the oral cavity. Particularly, when the lips of the wearer of the living-body monitoring device 1 are in the open state, a path from the living-body monitoring device 1 disposed on the palate side outside of the oral cavity is formed and thus a radio wave loss is remarkably decreased.

For example, the living-body monitoring device 1 may be disposed at a position between a molar and the tongue of the wearer in the oral cavity of the wearer of the living-body monitoring device 1 for use.

Fifth Embodiment

A living-body monitoring device according to a fifth embodiment of the present invention will be described below.

The living-body monitoring device 1 according to the fifth embodiment has the same configuration as the living-body monitoring device 1 according to the first embodiment except the following description. Accordingly, with the living-body monitoring device 1 according to the fifth embodiment, it is possible to achieve the same advantages as with the living-body monitoring device 1 according to the first embodiment except the following description.

Figures 10, 11:
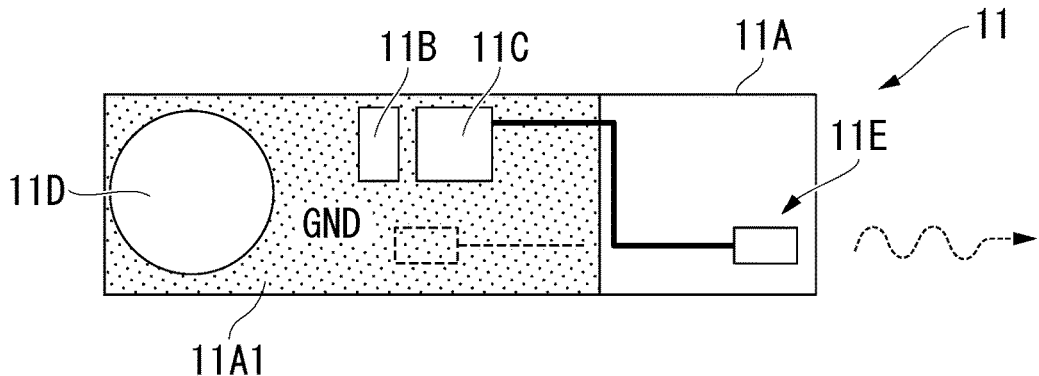
FIG. 10 is a diagram illustrating an example of an electronic device constituting part of a living-body monitoring device according to a fifth embodiment.
FIG. 11 is a diagram illustrating an example of a mirror image of an antenna of an electronic device which is formed in the electronic device of the living-body monitoring device according to the fifth embodiment.

FIG. 10 is a diagram illustrating an example of an electronic device 11 constituting part of the living-body monitoring device 1 according to the fifth embodiment. Specifically, FIG. 10(A) is a plan view of the electronic device 11, and FIG. 10(B) is a sectional view taken along line B-B of FIG. 10(A). FIG. 11 is a diagram illustrating an example of a mirror image of the antenna 11E of the electronic device 11 which is formed in the electronic device 11 of the living-body monitoring device 1 according to the fifth embodiment.

In the example illustrated in FIGS. 10 and 11, the electronic device 11 includes a circuit board 11A. The circuit board 11A is a 6-layer board including a copper-foil pattern layer 11A1 (see FIG. 10(B)).

For example, the circuit board 11A may be a board including layers other than 6 layers.

In the example illustrated in FIG. 10(B), the circuit board 11A includes a single copper-foil pattern layer 11A1. For example, the circuit board 11A may include a plurality of copper-foil pattern layers.

In the example illustrated in FIGS. 10 and 11, a sensor 11B, a control unit 11C, a battery 11D, and an antenna 11E are mounted on the circuit board 11A.

The antenna 11E is disposed at one end in the longitudinal direction (the right end in FIG. 10(A)) of the circuit board 11A and is a monopole antenna.

The circuit board 11A includes a first area 11A-1 which is an area in which the antenna 11E is disposed and a second area 11A-2 which is an area other than the first area 11A-1. Specifically, as illustrated in FIG. 10(B), the copper-foil pattern layer 11A1 provided in the second area 11A-2 is grounded.

For example, a plurality of copper-foil patterns may be disposed in the second area 11A-2, and one or more copper-foil pattern layers out of the plurality of copper-foil patterns disposed in the second area 11A-2 may be grounded.

In the example illustrated in FIGS. 10 and 11, the monopole antenna (the antenna 11E) is formed by combining a wired antenna (a metal wire) formed on the circuit board 11A (see FIG. 10(A)) and a chip antenna including a high dielectric material (high dielectrics). Specifically, the chip antenna of the monopole antenna (the antenna 11E) is connected to the control unit 11C via the wired antenna (a metal wire) and a power supply line. As described above, the copper-foil pattern layer 11A1 disposed in the second area 11A-2 is grounded. Accordingly, a mirror image of the monopole antenna (the wired antenna and the chip antenna) is formed in the second area 11A-2 as illustrated in FIG. 11. As a result, it is possible to enhance a radiation efficiency of the antenna.

As illustrated in FIGS. 10(A) and 10(B), the grounded copper-foil pattern layer 11A1 is disposed in the second area 11A-2 in which the antenna 11E is not provided. Accordingly, it is possible to increase the size in the longitudinal direction (the size in the right-left direction in FIGS. 10(A) and 10(B)) of the grounding area (that is, an area with the ground potential). As a result, it is possible to increase a percentage of the area of a part contributing to generation of a mirror image to the total area of the circuit board 11A and to maximize the radiation efficiency of the circuit board 11A with a minimal size.

Sixth Embodiment

A living-body monitoring device according to a sixth embodiment of the present invention will be described below.

The living-body monitoring device 1 according to the sixth embodiment has the same configuration as the living-body monitoring device 1 according to the fifth embodiment except the following description. Accordingly, with the living-body monitoring device 1 according to the sixth embodiment, it is possible to achieve the same advantages as with the living-body monitoring device 1 according to the fifth embodiment except the following description.

As described above, in the living-body monitoring device 1 according to the fifth embodiment, the monopole antenna (the antenna 11E) is formed by combining the wired antenna (a metal wire) formed on the circuit board 11A (see FIG. 10(A)) and the chip antenna including a high dielectric material (a high dielectrics).

On the other hand, in the living-body monitoring device 1 according to the sixth embodiment, the monopole antenna (the antenna 11E) does not include a wired antenna (a metal wire) and is a chip antenna including a high dielectric material (a high dielectrics).

In the living-body monitoring device 1 according to the sixth embodiment, similarly to the living-body monitoring device 1 according to the fifth embodiment, the copper-foil pattern layer 11A1 disposed in the second area 11A-2 is grounded, a mirror image of the monopole antenna (the chip antenna) is formed in the second area 11A-2. As a result, it is possible to enhance the radiation efficiency of the antenna.

In the living-body monitoring device 1 according to the sixth embodiment, similarly to the living-body monitoring device 1 according to the fifth embodiment, the grounded copper-foil pattern layer 11A1 is disposed in the second area 11A-2 in which the antenna 11E is not provided. Accordingly, it is possible to increase the size in the longitudinal direction of the grounding area (that is, an area with the ground potential). As a result, it is possible to increase the percentage of the area of a part contributing to generation of a mirror image to the total area of the circuit board 11A and to maximize the radiation efficiency of the circuit board 11A with a small size.

Seventh Embodiment

A living-body monitoring device according to a seventh embodiment of the present invention will be described below.

The living-body monitoring device 1 according to the seventh embodiment has the same configuration as the living-body monitoring device 1 according to the first embodiment except the following description. Accordingly, with the living-body monitoring device 1 according to the seventh embodiment, it is possible to achieve the same advantages as with the living-body monitoring device 1 according to the first embodiment except the following description.

Figure 12:
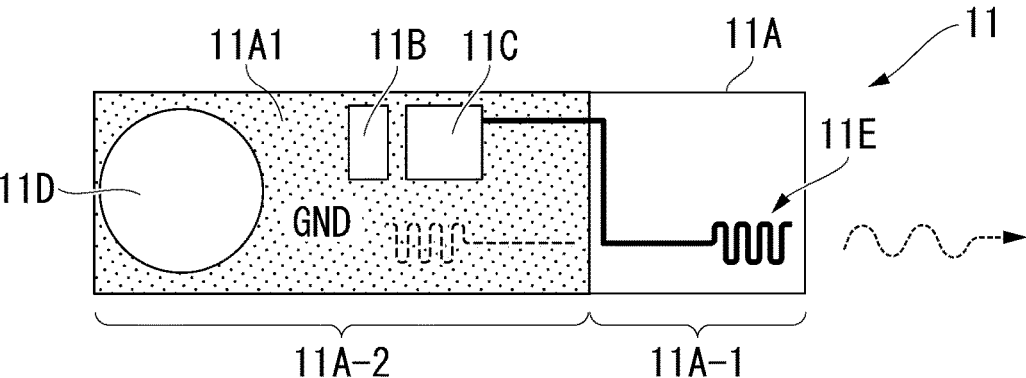
FIG. 12 is a diagram illustrating an example of a mirror image of an antenna of an electronic device which is formed in the electronic device of a living-body monitoring device according to a seventh embodiment.

FIG. 12 is a diagram illustrating an example of a mirror image of the antenna 11E of the electronic device 11 which is formed in the electronic device 11 of the living-body monitoring device 1 according to the seventh embodiment.

In the living-body monitoring device 1 according to the first embodiment, a mirror image (illustrated as an "image antenna" in FIG. 3) of the monopole antenna (the antenna 11E) having a linear shape is formed in the second area 11A-2 as illustrated in FIG. 3.

On the other hand, in the living-body monitoring device 1 according to the seventh embodiment, a mirror image of a monopole antenna (the antenna 11E) with a meander structure is formed in the second area 11A-2 as illustrated in FIG. 12.

Eighth Embodiment

A living-body monitoring device according to an eighth embodiment of the present invention will be described below.

The living-body monitoring device 1 according to the eighth embodiment has the same configuration as the living-body monitoring device 1 according to the first embodiment except the following description. Accordingly, with the living-body monitoring device 1 according to the eighth embodiment, it is possible to achieve the same advantages as with the living-body monitoring device 1 according to the first embodiment except the following description.

Figure 13:
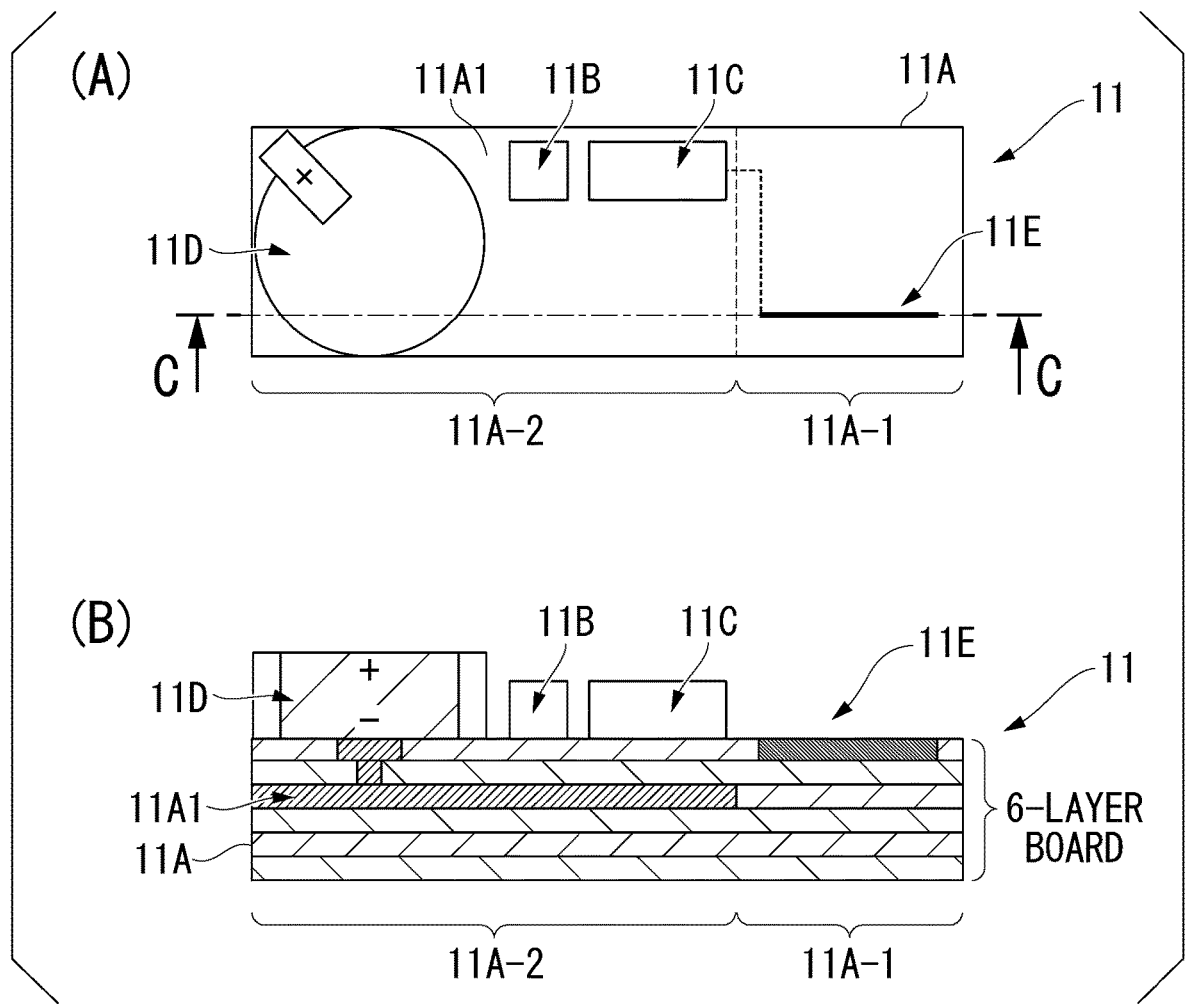
FIG. 13 is a diagram illustrating an example of an electronic device constituting part of a living-body monitoring device according to an eighth embodiment.

FIG. 13 is a diagram illustrating an example of an electronic device 11 constituting a part of the living-body monitoring device 1 according to the eighth embodiment. Specifically, FIG. 13(A) is a plan view of the electronic device 11 of the living-body monitoring device 1 according to the eighth embodiment, and FIG. 13(B) is a sectional view taken along line C-C of FIG. 13(A).

In the example illustrated in FIG. 13, the electronic device 11 includes a circuit board 11A. The circuit board 11A is a 6-layer board including a copper-foil pattern layer 11A1 (see FIG. 13(B)).

For example, the circuit board 11A may be a board including layers other than 6 layers.

In the example illustrated in FIG. 13(B), the circuit board 11A includes a copper-foil pattern layer 11A1 in an intermediate layer (a third layer from the uppermost in FIG. 13(B)).

The circuit board 11A includes a first area 11A-1 which is an area in which the antenna 11E is disposed and a second area 11A-2 which is an area other than the first area 11A-1. Specifically, as illustrated in FIG. 13(B), the copper-foil pattern layer 11A1 provided in the second area 11A-2 (the copper-foil pattern layer 11A1 which is the third layer from the uppermost in FIG. 13(B)) is grounded.

Ninth Embodiment

A living-body monitoring device according to a ninth embodiment of the present invention will be described below.

The living-body monitoring device 1 according to the ninth embodiment has the same configuration as the living-body monitoring device 1 according to the first embodiment except the following description. Accordingly, with the living-body monitoring device 1 according to the ninth embodiment, it is possible to achieve the same advantages as with the living-body monitoring device 1 according to the first embodiment except the following description.

Figure 14:
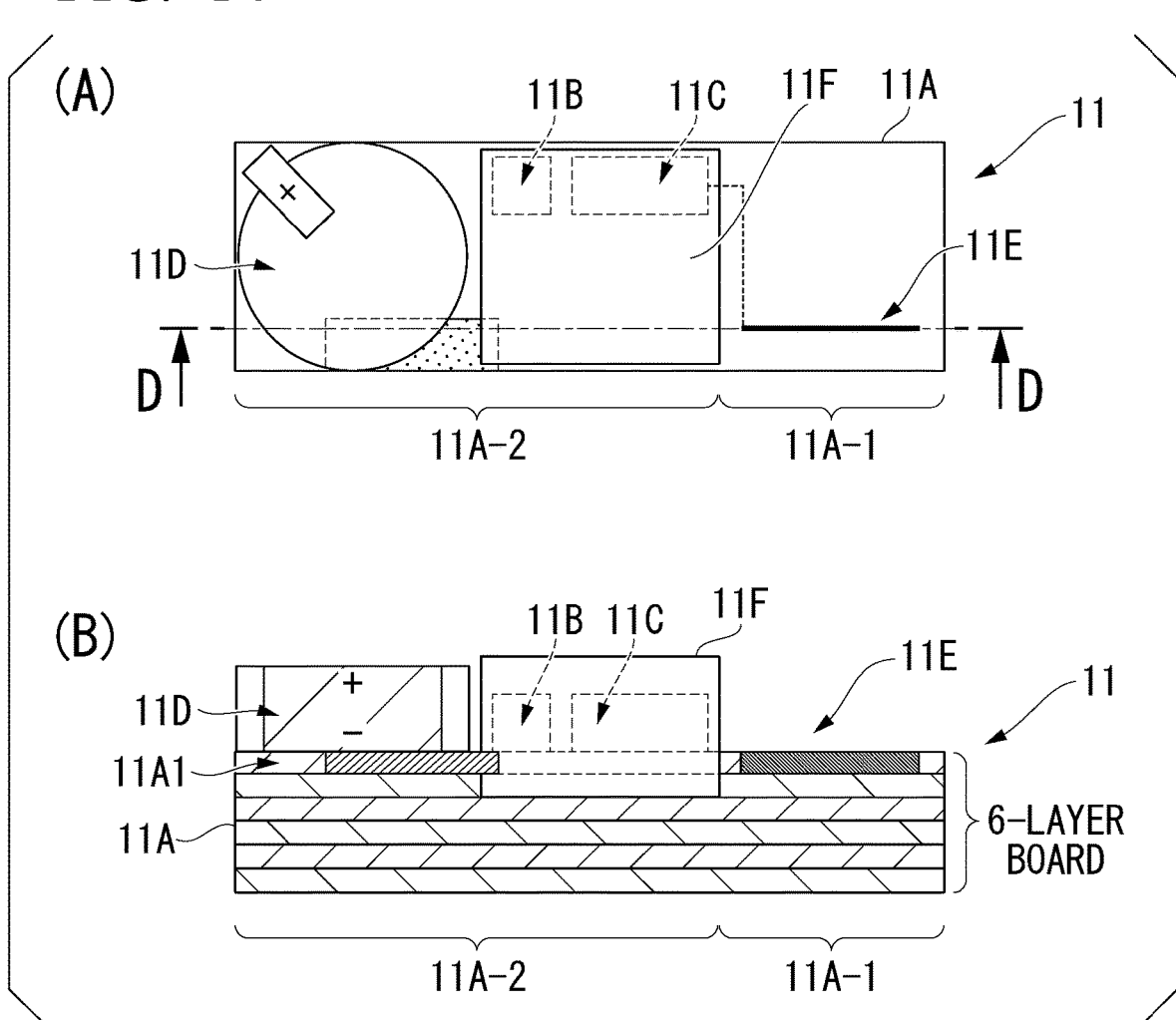
FIG. 14 is a diagram illustrating an example of an electronic device constituting part of a living-body monitoring device according to a ninth embodiment.

FIG. 14 is a diagram illustrating an example of an electronic device 11 constituting a part of the living-body monitoring device 1 according to the ninth embodiment. Specifically, FIG. 14(A) is a plan view of the electronic device 11 of the living-body monitoring device 1 according to the ninth embodiment, and FIG. 14(B) is a sectional view taken along line D-D of FIG. 14(A).

In the example illustrated in FIG. 14, the electronic device 11 includes a circuit board 11A. The circuit board 11A includes a copper-foil pattern layer 11A1. The copper-foil pattern layer 11A1 is grounded. A sensor 11B, a control unit 11C, a battery 11D, an antenna 11E, and a metal cover 11F are mounted on the circuit board 11A. The metal cover 11F covers a part of the circuit board 11A and is grounded.

MODIFIED EXAMPLES

In the living-body monitoring devices 1 according to the first to ninth embodiments, the antenna 11E is a monopole antenna. In some modified examples of the embodiments, the antenna may be formed as a copper-foil pattern on the circuit board 11A (a printed circuit board). When the antenna is formed as a copper-foil pattern, the antenna may be an inverted-L antenna or an inverted-F antenna. In any case, a direction in which a mirror image is formed has to be parallel to the longitudinal direction of the circuit board 11A. A combined antenna of a copper-foil pattern and a chip antenna may be used.

While modes for carrying out the present invention have been described above with reference to embodiments, the present invention is not limited to the embodiments and can be subjected to various modifications and replacements without departing from the gist of the present invention. The configurations of the aforementioned embodiments and examples may be combined.

The invention claimed is:

1. A living-body monitoring device comprising:
an electronic device including a circuit board; and
a living-body wearing instrument enclosing the electronic device,
wherein a control unit, a battery, and an antenna are mounted on the circuit board,
wherein the circuit board has a length in a longitudinal direction and a length in a transverse direction and includes one or more copper-foil pattern layers,
wherein the antenna is disposed at one end in the longitudinal direction of the circuit board,
wherein the circuit board includes a first area which is an area in which the antenna is disposed and a second area which is an area other than the first area, and
wherein at least one copper-foil pattern layer of the one or more copper-foil pattern layers that is disposed in the second area is grounded.

2. The living-body monitoring device according to claim 1, wherein a sensor is mounted on the circuit board,
wherein the living-body wearing instrument is an intraoral instrument, and
wherein the living-body monitoring device is disposed in an oral cavity such that the longitudinal direction of the circuit board is aligned with a row of teeth.

3. The living-body monitoring device according to claim 2, wherein the intraoral instrument is an orthodontic appliance, a denture, or an implant.

4. The living-body monitoring device according to claim 2, wherein the control unit sets a first radiated radio wave intensity which is an intensity of radio waves radiated from the antenna when the living-body monitoring device is disposed inside of the oral cavity and a second radiated radio wave intensity which is an intensity of radio waves radiated from the antenna when the living-body monitoring device is disposed outside of the oral cavity to be different, and wherein a ratio of the second radiated radio wave intensity to the first radiated radio wave intensity is equal to or greater than 0.1 and equal to or less than 0.2.

5. The living-body monitoring device according to claim 2, wherein the antenna is located on a lip side in the oral cavity when the living-body monitoring device is disposed in the oral cavity.

6. The living-body monitoring device according to claim 2, wherein a main lobe of a radiation pattern of the antenna is directed outside of the oral cavity via the lips when the living-body monitoring device is disposed in the oral cavity.

7. The living-body monitoring device according to claim 1, wherein the antenna is a monopole antenna.

8. The living-body monitoring device according to claim 1, wherein the battery is disposed on a side opposite to the antenna with the control unit interposed therebetween.

9. The living-body monitoring device according to claim 1, wherein the circuit board includes a long side and a short side, and wherein a ratio of a length of the long side to a length of the short side is equal to or greater than 2.

10. The living-body monitoring device according to claim 9, wherein the short side is less than 15 mm the long side is less than 30 mm and the ratio of the length of the long side to the length of the short side is equal to or greater than 3.5 and equal to or less than 7.

11. The living-body monitoring device according to claim 1, wherein the living-body monitoring device is disposed on a palate side in the oral cavity.

12. The living-body monitoring device according to claim 1, wherein a sensor is mounted on the circuit board, wherein the living-body wearing instrument is an intraoral instrument, wherein the sensor detects an open/closed state of the lips of a wearer of the living-body monitoring device, and wherein the control unit switches a communication status according to the open/closed state of the lips of the wearer of the living-body monitoring device detected by the sensor.

* * * * *